United States Patent
Uchida et al.

(10) Patent No.: US 7,507,967 B2
(45) Date of Patent: Mar. 24, 2009

(54) INFRARED GAS DETECTOR

(75) Inventors: Kouji Uchida, Kariya (JP); Takahiko Yoshida, Okazaki (JP)

(73) Assignee: DENSO CORPORATION, Kariya (JP)

( * ) Notice: Subject to any disclaimer, the term of this patent is extended or adjusted under 35 U.S.C. 154(b) by 258 days.

(21) Appl. No.: 11/334,434

(22) Filed: Jan. 19, 2006

(65) Prior Publication Data

US 2006/0219923 A1  Oct. 5, 2006

(30) Foreign Application Priority Data

Mar. 30, 2005  (JP) .............................. 2005-099841

(51) Int. Cl.
*G01J 5/04*  (2006.01)
(52) U.S. Cl. ..................................... 250/343
(58) Field of Classification Search ................ 250/343
See application file for complete search history.

(56) References Cited

U.S. PATENT DOCUMENTS 3,656,841 A * 4/1972 Heinonen, Jr. ............... 352/45
5,973,326 A * 10/1999 Parry et al. .................. 250/343
2005/0030628 A1* 2/2005 Wagner et al. .............. 359/573

FOREIGN PATENT DOCUMENTS

JP  A-2001-228086  8/2001

* cited by examiner

*Primary Examiner*—David P Porta
*Assistant Examiner*—Shun Lee
(74) *Attorney, Agent, or Firm*—Posz Law Group, PLC

(57) ABSTRACT

An infrared gas detector includes an infrared light source for emitting infrared light, an infrared sensor for detecting the infrared light from the infrared light source, and a housing having a gas cell which accommodates the infrared light source and the infrared sensor. The internal surface of the gas cell is defined as an ellipsoidal surface. The positions of the infrared light source and the infrared sensor are respectively determined based on two different focal points of the ellipsoidal surface of the gas cell to efficiently focus the infrared light from the infrared light source on the infrared sensor.

11 Claims, 2 Drawing Sheets

INFRARED GAS DETECTOR

CROSS REFERENCE TO RELATED APPLICATION

This application is based upon, claims the benefit of priority of, and incorporates by reference the contents of Japanese Patent Application No. 2005-099841 filed Mar. 30, 2005.

FIELD OF THE INVENTION

The present invention relates to gas detectors, and specifically to an infrared gas detector that uses an infrared light source to emit infrared light and an infrared sensor that detects the concentration of a target gas by using light absorption characteristics that are determined when the infrared light propagates through the target gas.

BACKGROUND OF THE INVENTION

An infrared gas detector such as the one disclosed in JP-A-2001-228086 and as shown in FIG. 3 is known. Such a gas detector is equipped with an incandescent electric bulb 1 as an infrared light source, infrared sensing elements 2a and 2b that form an infrared sensor, and a gas cell 4 to which is introduced a target gas to be measured. The target gas is introduced inside the gas cell 4 through vent holes 5 provided in the gas cell 4. The incandescent electric bulb 1 radiates infrared light of a broad wavelength. The infrared light propagates through the target gas introduced into the gas cell 4 and is incident on the infrared sensing elements 2a and 2b after passing through a multi-wavelength selection filter and a band pass filter 3. The infrared sensing elements 2a and 2b sense the infrared light at a desired wavelength, which is adjusted by the multi-wavelength selection filter and the band pass filter 3, and output detection signals corresponding to the intensity of the received infrared light.

As the infrared light propagates through the target gas, infrared light at a certain wavelength is absorbed by the target gas. The intensity of the infrared light that is absorbed by the target gas varies in accordance with the concentration of the target gas, and the wavelength at which the infrared light is absorbed is dependent on the class of the target gas. Therefore, by adjusting the multi-wavelength selection filter and the band pass filter 3 based on the particular target gas, the output signals of the infrared sensing elements 2a and 2b may correspond to the absorption characteristics of the infrared light, thereby enabling the concentrations of the target gases to be detected.

As shown in FIG. 3, the gas cell 4 is provided with a concave paraboloidal reflector 6. The concave paraboloidal reflector 6 reflects infrared light scattered in the direction opposite the sensing elements 2a and 2b, and thereby directs the infrared light in the direction of the sensing elements 2a and 2b.

However, in the case of the above infrared gas detector, the rays of the infrared light emitted from the incandescent electric bulb 1 become parallel to the side wall of the cylindrical gas cell 4 as a result of being reflected by the concave paraboloidal reflector 6, and irradiate the infrared sensing elements 2a and 2b. When the rays are parallel to the side wall of the gas cell 4, some of rays irradiate regions of the detector other than where the infrared sensing elements 2a and 2b are disposed, and therefore efficient radiation of infrared light from the incandescent bulb 1 cannot be obtained.

SUMMARY OF THE INVENTION

In view of the foregoing, it is an object of the present invention to provide an infrared gas detector in which infrared light efficiently irradiates an infrared sensor.

An infrared gas detector according to one aspect of the present invention includes an infrared light source for emitting infrared light, an infrared sensor for detecting the infrared light emitted from the infrared light source, and a housing having a gas cell which accommodates the infrared light source and the infrared sensor therein, the internal surface of the gas cell being defined as an ellipsoidal surface.

Moreover, it may be preferable for the infrared light source and the infrared sensor to be located at respective positions determined on the basis of two different focal points in the ellipsoidal gas cell. Specifically, the ellipsoid has two focal points, and has a characteristic that light emitted from one focal point may be focused on the other focal point. Accordingly, disposing the infrared light source and the infrared sensor at respective positions determined on the basis of two different focal points in the ellipsoidal gas cell can make it possible to efficiently irradiate the infrared sensor with the infrared light from the infrared light source.

BRIEF DESCRIPTION OF THE DRAWINGS

The above and other objects, features and advantages of the present invention will become more apparent from the following description of the preferred embodiments given with reference to the attached drawings, wherein.

DETAILED DESCRIPTION OF THE PREFERRED EMBODIMENT

Preferred embodiments according to the present invention will be described hereunder with reference to the accompanying drawings.

Figure 1:
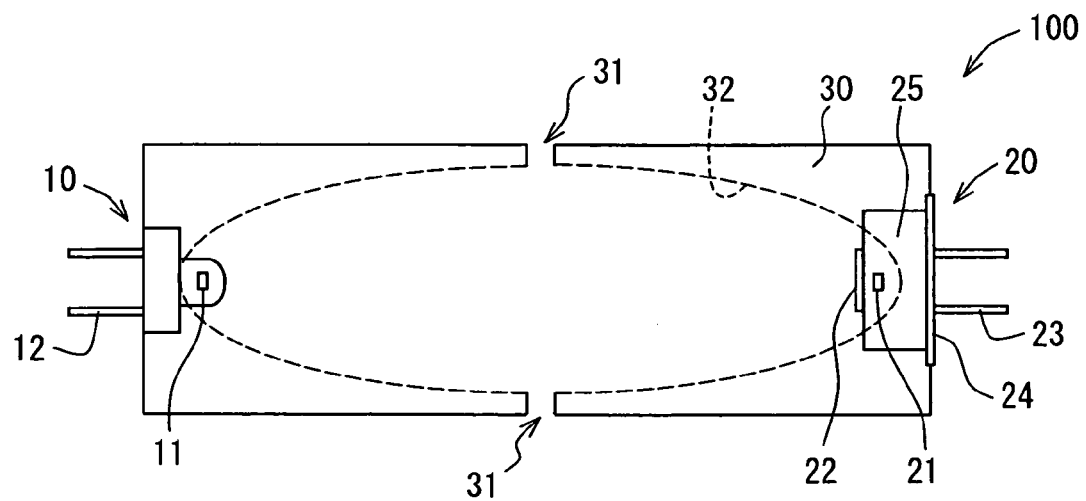
FIG. 1 is a schematic cross-sectional view showing the construction of an infrared gas detector according to an exemplary embodiment of the present invention.

FIG. 1 shows the construction of an infrared gas detector 100 according to an exemplary embodiment of the present invention. As shown in FIG. 1, the infrared gas detector 100 primarily includes an infrared light source 10, an infrared sensor 20 and a housing 30. The infrared gas detector 100 detects the concentration of a target gas, such as $CO_2$ gas, based on the absorption characteristics of infrared light at a certain wavelength when the infrared light propagates through the target gas.

The infrared light source 10 includes an infrared light emitting device 11 and a connector 12. The infrared light emitting device 11 is an infrared radiation source such as, for example, a light-emitting diode (LED), a semiconductor laser or an incandescent lamp. That is, any type of infrared radiation source, such as a broadband infrared light source or a narrowband infrared light source, may be utilized as the infrared light emitting device 11 if it is capable of emitting infrared light. When a broadband infrared light source is utilized, a band pass filter may be contained within the infrared light source 10 so that only infrared light having a desired wavelength propagates through the target gas. The connector 12 electrically connects the infrared light emitting device 11 with a driver circuit (not shown) for driving the infrared light emitting device 11.

The infrared sensor 20 includes an infrared sensing device 21, a band pass filter 22 and a connector 23. The infrared sensing device 21, which may be a thermopile detector, a bolometric detector, a pyroelectric detector or any other infrared detector, outputs a signal indicative of the intensity of infrared light that it senses. The signal is output through the connector 23 to an outside processing circuit (not shown).

The infrared sensing device 21 is located within an interior space of the infrared sensor 20. The interior space is formed by a pedestal 24 and a cap 25 assembled on the pedestal 24. The band pass filter 22 is fit on the cap 25 to selectively transmit infrared light of a specific wavelength, which is adjusted to an infrared absorption wavelength for the class of the target gas. The cap 25 is configured, in association with the band pass filter 22, so as to restrict the transmission of the infrared light emitted from the infrared light emitting device 11 and incident on the limited region where the infrared sensing device 21 is located to a specific wavelength. In this embodiment, the cap 25 is constructed so that a region other than the region on which the band pass filter 22 is disposed is shielded from the infrared light. Incidentally, if the infrared light source 10 is configured to emit infrared light only at a desired specific wavelength, the band pass filter 22 may be omitted.

The housing 30 has vent holes 31 for introducing a target gas, such as $CO_2$ gas, into a gas cell 32. In this embodiment, there are two vent holes 31, one of which serves as an inlet port and the other of which serves as an outlet port. Of course, other configurations may be applicable for the introduction of the target gas. The above-mentioned infrared light source 10 and the infrared sensor 20 are installed in the housing 30.

The housing 30 is formed from a material having a high infrared reflectance such as, for example, aluminum. Therefore, the gas cell 32 has a highly reflective surface relative to the infrared light. The gas cell 32 is contoured so as to define the internal surface of the housing 30 as an ellipsoidal surface. The housing 30 of this embodiment may be produced by, for example, forming semi-ellipsoidal housing components by aluminum die-casting and then assembling the components.

Here, in the presently described embodiment, it may be preferable for the infrared light source 10 and the infrared sensor 20 to be located at respective positions determined on the basis of two different focal points in the ellipsoidal gas cell 32.

Figure 2:
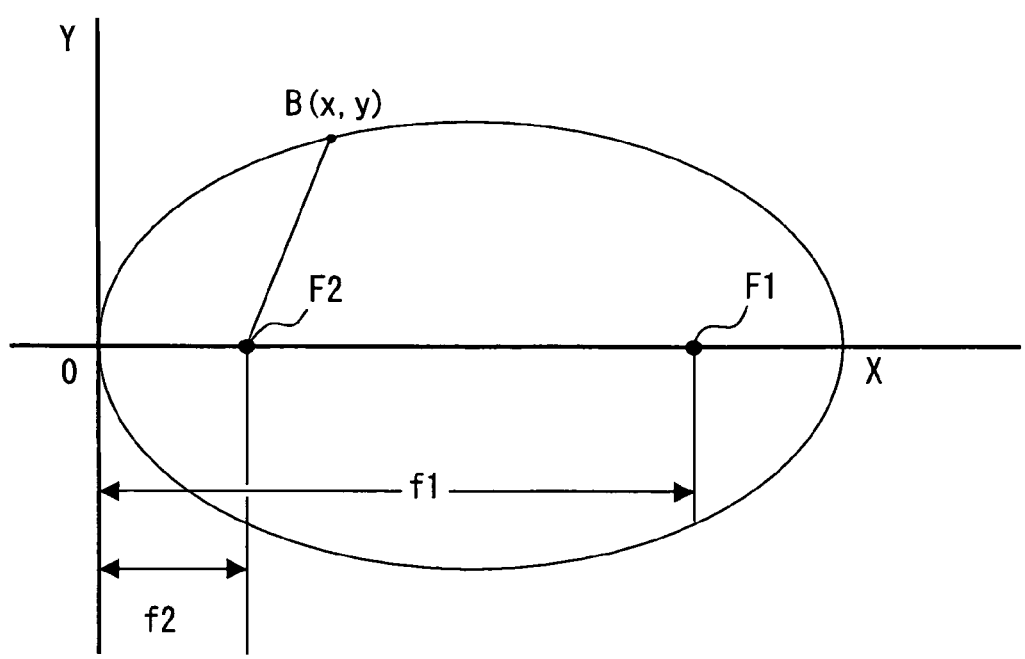
FIG. 2 is a diagram that identifies the focal points of the ellipsoidal gas cell of the gas detector shown in FIG. 1.

The ellipsoidal gas cell 32 has two focal points, and has a characteristic that light emitted from one focal point is focused on the other focal point. As shown in FIG. 2, the focal points F1 and F2 of an ellipsoid exist on a central axis thereof. If the distances from the origin in X-Y coordinates to the focal points F1 and F2 are defined as focal lengths f1 and f2, respectively, the relationship between the focal lengths f1 and f2 is expressed by equation (1) through equation (3) as follows.

$$(a-x)^2/a^2 + y^2/b^2 = 1 \quad (1)$$

$$2a = f1 + f2 \quad (2)$$

$$b^2 = f1 \times f2 \quad (3)$$

(Here, a and b are positive integers.)

Accordingly, when the infrared light source 10 and the infrared sensor 20 are disposed at the positions determined on the basis of two different focal points in the ellipsoidal gas cell 32, it may be possible to efficiently irradiate the infrared sensing device 21 with the infrared light from the infrared light emitting device 11. In other words, it may be preferred that the infrared light source 10 and the infrared sensor 20 are installed in the housing 30 so that the respective positions of the infrared light emitting device 11 and the infrared sensing device 21 are controlled to be at the two different focal points in the ellipsoidal gas cell 32.

In the presently described embodiment, since the infrared sensor 20 includes the band pass filter 22 as described above, the position of the infrared sensor 20, or, more specifically, the position of the infrared sensing device 21, may be determined taking into consideration a refractive characteristic of the band pass filter 22. Therefore, the position of the infrared sensor 20 is adjustable in accordance with the refractive index of the band pass filter 22 so that the infrared sensing device 21 is disposed between the band pass filter 22 and the focal point, which is the reference point for the infrared sensor 20. By doing so, the effects of the refractive characteristic of the band pass filter 22 may be minimized, and thus efficient infrared irradiation onto the infrared sensing device 21 may be achieved.

Similarly, if the infrared light source 10 is designed to include a band pass filter, it may be preferred that the position of the infrared light emitting device 11 is shifted from the focal point as the reference point for the infrared light source 10 in accordance with the refractive index of the band pass filter. Incidentally, in case any band pass filters are omitted, it may be preferred for the infrared light-emitting device 11 or the infrared sensing device 20 to be disposed at a corresponding focal point in the ellipsoidal gas cell 32.

Figure 3:
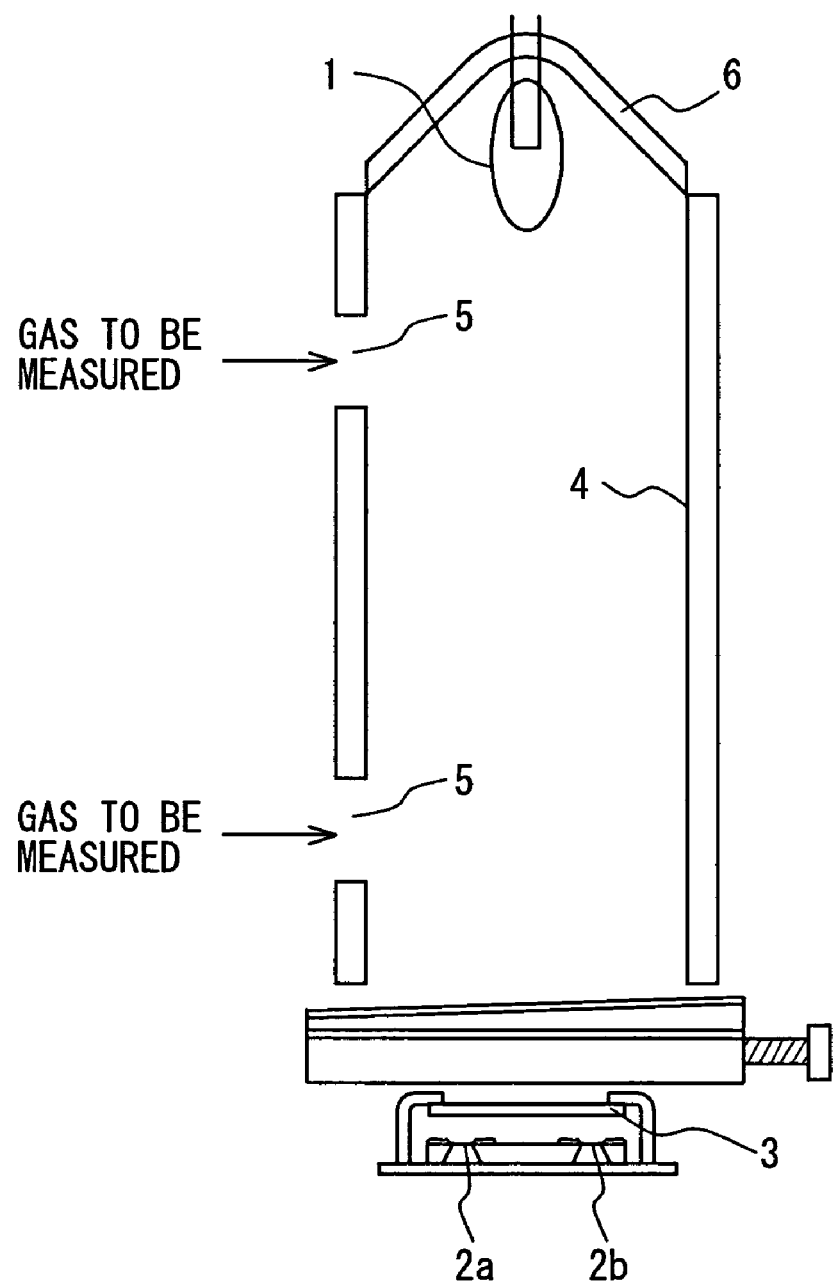
FIG. 3 is a schematic cross-sectional view showing the construction of a conventional infrared gas detector.

Furthermore, in the above exemplary embodiment, a gas cell has been described as having an ellipsoidal shape. However, even if a gas cell has a cylindrical shape such as the conventional infrared gas detector of FIG. 3, efficient detection may be achieved by designing the gas cell so that an inner wall at the side of the infrared sensor has a curved surface, such as a paraboloidal surface. As a result, infrared light propagating through the target gas may be reflected by the paraboloidal surface and focused on the infrared sensing device.

While the invention has been described with reference to preferred embodiments thereof, it is to be understood that the invention is not limited to the preferred embodiments and constructions. The invention is intended to cover various modifications and equivalent arrangements. In addition, the various combinations and configurations, which are preferred, other combinations and configurations, including more, less or only a single element, are also within the spirit and scope of the invention.

What is claimed is:

1. An infrared gas detector comprising:
   an infrared light source for emitting infrared light;
   an infrared sensor for detecting the infrared light emitted from the infrared light source;
   a housing having an ellipsoidal interior surface that defines an ellipsoidal interior space in which the infrared light source and the infrared sensor are disposed and a target gas to be measured is introduced, the infrared light source and the infrared sensor being positioned relative to two respective focal points of the ellipsoidal interior space; and
   a pair of ports for introducing the target gas to the ellipsoidal interior space, wherein the pair of ports is disposed in the housing between the infrared light source and the infrared sensor so that the pair of ports is disposed on a minor axis of the ellipsoidal interior space.

2. The infrared gas detector according to claim 1, wherein:

the infrared light source has an infrared light emitting device;

the infrared sensor has an infrared sensing device;

the infrared light emitting device is disposed based on a first focal point of the ellipsoidal interior space; and the infrared sensing device is disposed based on a second focal point of the ellipsoidal interior space, the first and second focal points being different from each other.

3. The infrared gas detector according to claim 2, wherein:

the infrared light source has a band pass filter to make the infrared light propagating through the target gas a specific wavelength; and the infrared light emitting device is disposed to be shifted from the first focal point in accordance with a refractive characteristic of the band pass filter.

4. The infrared gas detector according to claim 2, wherein:

the infrared sensor has a band pass filter to make the infrared light irradiating the infrared sensing device a specific wavelength; and the infrared sensing device is disposed to be shifted from the second focal point in accordance with a refractive characteristic of the band pass filter.

5. An infrared gas detector comprising:

an infrared light source for emitting infrared light;

an infrared sensor for detecting the infrared light from the infrared light source; and a housing having an interior space in which the infrared light source and the infrared sensor are disposed, and a pair of ports for introducing a target gas to be measured to interior space between the infrared light source and the infrared sensor, wherein the interior space of the housing having a first curved surface and a second curved surface, wherein the first curved surface is for directing the infrared light in a direction of the infrared sensor, wherein the second curved surface is for collecting the infrared light on the infrared sensor, wherein the infrared light source is disposed on a first focal point of the first curved surface;

wherein the infrared sensor is disposed on a second focal point of the second curved surface, and wherein the pair of ports is disposed in the housing between the infrared light source and the infrared sensor so that the pair of ports is disposed on a minor axis of the interior space.

6. The infrared gas detector according to claim 5, wherein:

the infrared light source has an infrared light emitting device; and the infrared sensor has an infrared sensing device.

7. The infrared gas detector according to claim 6, wherein:

the infrared light source has a band pass filter to make the infrared light propagating through the target gas a specific wavelength; and the infrared light emitting device is disposed to be shifted from the first focal point in accordance with a refractive characteristic of the band pass filter.

8. The infrared gas detector according to claim 6, wherein:

the infrared sensor has a band pass filter to make the infrared light irradiating the infrared sensing device a specific wavelength; and the infrared sensing device is disposed to be shifted from the second focal point in accordance with a refractive characteristic of the band pass filter.

9. An infrared gas detector comprising:

an infrared sensing device for detecting infrared light;

an infrared light emitter for irradiating the infrared sensing device through a space provided between the infrared sensing device and the infrared light emitter, the space being supplied with a target gas to be measured;

an infrared reflector that collects the infrared light from the infrared light emitter onto the infrared sensing devices; and a pair of ports for introducing the target gas to the space, wherein the infrared light emitter is disposed on one of two focal points of the space;

wherein the infrared sensing device is disposed on the other of the two focal points of the space, and wherein the pair of ports is disposed between the infrared light emitter and the infrared sensing device so that the pair of ports is disposed on a minor axis of the space.

10. The infrared gas detector according to claim 9, wherein the infrared reflector comprises an ellipsoidal surface that encompasses both the infrared sensing device and the infrared light emitter.

11. The infrared gas detector according to claim 9, wherein the infrared reflector comprises a first curved surface for directing the infrared light in a direction of the infrared sensing device, and a second curved surface for collecting the infrared light on the infrared sensing device.

* * * * *